United States Patent [19] [11] 3,970,852
Richey et al. [45] July 20, 1976

[54] PROCESS AND APPARATUS FOR SCANNING SECTIONS OF RADIATION

[75] Inventors: Joseph B. Richey, Shaker Heights; Robert H. Wake, Warrensville Heights; John T. Keller, Willoughby, all of Ohio

[73] Assignee: Ohio Nuclear, Inc., Solon, Ohio

[22] Filed: July 8, 1974

[21] Appl. No.: 486,398

[52] U.S. Cl. .............................. 250/363 S; 250/366; 250/369
[51] Int. Cl.² ........................................ G01T 1/164
[58] Field of Search .................... 250/363, 366, 369

[56] References Cited
UNITED STATES PATENTS

| | | | |
|---|---|---|---|
| 3,573,458 | 4/1971 | Anger | 250/369 X |
| 3,839,641 | 10/1974 | Cooke et al. | 250/369 |
| 3,860,821 | 1/1975 | Barrett | 260/366 X |

*Primary Examiner*—Archie R. Borchelt
*Attorney, Agent, or Firm*—Fay & Sharpe

[57] ABSTRACT

The process of this invention includes detecting gamma radiation with a radiation sensing device, converting the gamma radiation to light radiation, viewing the light radiation with photomultiplier tubes and giving electrical impulses in response thereto. The impulses are operated on to correct for any distortion and to give an indication of the relation to location of the radiation. An area of interest, for the purpose of scanning, is selected and electronically masked. During a first pass, initial scanning is done electronically without physical movement of the radiation sensing device head. After initial electronic scanning, a detector head passes over the radiation of interest while sensing radiation. At the end of the mechanical movement, an area of radiation is again electronically scanned. A cot supporting the section of radiation is moved transverse to the longitudinal movement of the head after the first pass. A scan in the opposite direction occurs similar to that in the first direction. The radiation is correlated between the first scan and the second scan. In order to reduce artifacts, the perimeters of the areas under consideration are oscillated with a saw-tooth wave.

The apparatus includes a radiation sensing device for scanning a section of radiation, normally an irradiated patient. The radiation sensing device includes a camera detection head and has a collimator which channels radiation, normally gamma radiation, from the patient to a scintillation crystal operatively attached thereto. The scintillation crystal converts gamma radiation to light radiation which is noted by photomultiplier tubes viewing the scintillation crystal. Electrical responses given by the photomultiplier tubes are operatively attached to means for operating on the electrical impulses to create a signal which gives an indication of the relative location of the radiation. A drive means moves the camera head in a longitudinal direction along a cot supporting the patient. At each end of the mechanical movement of the head, an electronic scanner views the ends of the section of radiation under consideration. Appropriate mechanical drive means moves or indexes the table supporting the patient in a direction transverse to the longitudinal movement of the detector head. A means for blending the radiation received from multiple passes of the detector head includes an electronic mask with oscillating sides. In this manner, multiple passes can be blended without substantial artifacts. A means for sequencing events governs the proper order of events.

32 Claims, 16 Drawing Figures

FIG. 4

PROCESS AND APPARATUS FOR SCANNING SECTIONS OF RADIATION

BACKGROUND OF THE INVENTION

This invention is an improvement of application Ser. No. 370,163, filed June 14, 1973 and application Ser. No. 396,494, filed Sept. 12, 1973 which are hereby incorporated by reference.

Rectilinear scanners use a single line of radiation and are moved along a square wave path to sense patterns of radiation. The rectilinear scanner has the advantage of being able to view the entire body of a patient, and the disadvantage of taking about 45 minutes to do so. Patient discomfort, movement and signal inaccuracies often result from the time necessary for such a scan.

For small area studies, what has commonly become known as a scintillation camera has a distinct advantage over a rectilinear scanner. The camera views an entire area of radiation simultaneously and, thus, greatly reduces the time necessary for the patient to remain motionless. A previous disadvantage of a camera over the rectilinear scanner was its inability to study large sections of radiation. A natural evolution for the camera was its transition into a type of camera-scanner in which the area of camera view traversed the section of radiation, e.g., a whole body scan. Because of the greater area of the detecting head of the scintillation camera as compared to a rectilinear scanner, the time of an entire body scan was reduced from about 45 minutes to 10 minutes. This significant decrease in the amount of time is a substantial benefit since it increases potential patient utilization and permits greater patient comfort and accuracy.

One of the problems encountered in having a camera scan is the correlation of data. The detector head of the camera is not large enough to encompass the entire width of some sections of radiation and, as a result, the camera must make multiple passes in order to complete a scan. Correlation of the information from the multiple passes must be precise or artificial indications of radiation, called artifacts, will appear. In particular, if the passes overlap, some areas will be reviewed twice and if the passes are separated, areas could be missed.

In order to reduce the artifacts from multiple passes, the present invention has derived a means for correlating the adjacent sides of a scanning area. The scanning area is defined by an electronic mask which allows the camera to display only the scintillations in a given area. The area may be a rectangle, a parallelogram, square or other shape. This invention provides for the oscillation of the sides parallel to the longitudinal sides of the pass at a given frequency and thus eliminates distinct edges to information received during the pass. When the second or subsequent pass occurs, the same oscillation is used and the information is matched with that of the first pass so that the adjacent edges combine in a feathered effect which does not give detectable artifacts or lines of demarcation.

The scanning camera also must provide uniform exposure of the detector head to the section of radiation under study. In order to equalize radiation exposure, the detector head of the camera previously had to start beyond the initial end of the section of radiation and pass completely over the other end. Thus, facilities were required to permit the detector head to move completely beyond the radiation under study. The overhang of the detector head was an annoying problem in the hospital. Space utilization on either side of the scanning camera became impossible and physical contact with the overhanging section could cause inaccuracies in tests and potential damage to the camera and injury to the operator.

In order to avoid camera overhang, the present invention proposes to limit the mechanical movement of the camera head to a path above the section of radiation it views. That is, the camera head stays above the cot on which the patient is lying. While the undesirable overhang of the camera is avoided, compensation must be made for the reduced exposure time of the head to the ends of the section of radiation. A simple mechanical pass moves the head away from its starting position before adequate radiation can be observed. In order to provide the same amount of exposure of the head to all areas of the section of radiation, an electronic scan is provided at each end of a mechanical scan. When the first pass is initiated, an electronic scan occurs. It operates similar to a sliding lid gradually opening on a box. The electronic scan is timed to correspond with the mechanical scan so that no artifacts are created by the transfer from electrical to mechanical scans. When the electronic scan is complete, the head mechanically moves and traverses the length of the section of radiation under consideration. When the head reaches the end of the section of radiation, instead of having to pass completely over it as in the prior art, it is able to stop and another electronic scan continues in a manner similar to closing a sliding lid on a box container. At the end of the first pass, the support means for the section of radiation, i.e. the cot on which the patient is lying, is indexed or moved transverse to the longitudinal scan direction. The electronic scan again occurs but in the opposite direction, the mechanical scan is actuated, the head moves the length of the section of radiation and an electronic scan again occurs. Similar additional passes can be made to complete the scan.

SUMMARY OF THE INVENTION

The process of scanning a section of radiation includes detecting radiation and giving electrical impulses in response thereto. The electrical impulses are operated on in order to give an indication of the relative location of the radiation. Scanning the section of radiation includes selecting an area of radiation in which the radiation is to be detected on and operated on in order to determine the radiation's relative location and oscillating at least part of the perimeter of the area of radiation being operated on in order to subsequently match the perimeters of such area in multiple passes. The scanning further includes making multiple passes with the area of radiation and assimilating the perimeters of the areas in order to substantially eliminate artifacts as a result of the multiple passes. Electronic scans are made at the ends of each pass.

A radiation sensing device for scanning a portion of radiation including a means for detecting radiation and giving electrical impulses in response thereto. A means for operating on the electrical impulses gives an indication of the relative location of the radiation. A means for scanning a section of radiation includes a means for selecting an area of radiation having a perimeter and a means for varying at least part of the perimeter of the area of radiation being operated on. A means for controlling the means for detecting the means for scanning governs the sequencing of events in order that the means for detecting can make multiple passes over

BRIEF DESCRIPTION OF THE DRAWINGS

FIG. 4 is a block diagram of the system of this invention;

DETAILED DESCRIPTION OF THE DRAWINGS

General System

Figure 1:
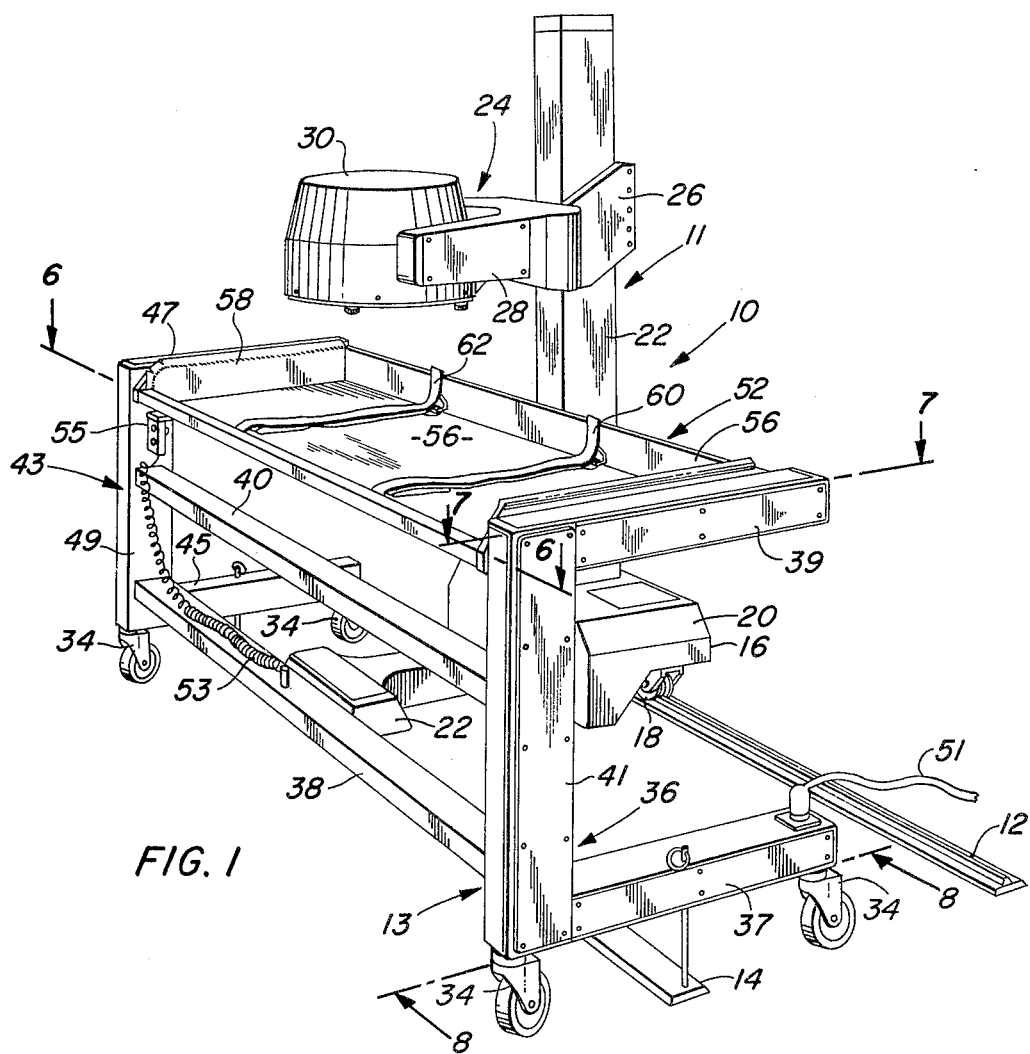
FIG. 1 is a perspective view of the scanning camera head and movable support means of this invention.

As illustrated in FIG. 1, this invention relates to a scanning radiation sensing device 10 having a detection means 11 and a support means 13. The detection means 11 includes a V-shaped rail 12 and a rail 14 on which a stand 16 moves longitudinally on rollers 18, one of which is shown. The other rollers are covered by plates 20 and 22. The rail 12 is V-shaped for use with a camera encoder described hereinafter. A column 22 projects upwardly from the stand 16 and holds a brace 26 which is movably mounted in a conventional manner for traversing the length of the column 22. The brace 26 is operatively connected to a yoke 28 which pivotally supports a detector head 30. The detector head 30 can and often is placed under the cot 52.

The support means 13 for a section of radiation includes caster wheels 34 supporting a C-shaped frame 36 having two horizontal members 37 and 39 connected by a vertical member 41. A second C-shaped frame 43 has similar horizontal members 45 and 47 and a connecting vertical member 49. Pins 50 and 51 in frames 36 and 43, respectively, prevent the support means from rolling relative to the rail 14 by fitting in openings in the rail 14. The C-shaped frames 36 and 43 are spaced and connected by horizontal braces 38 and 40. A cot 52 is mounted on the frames 36 and 43 and moves in a direction away from column 22, i.e. transverse from the longitudinal movement of the detecting means 11. The cot 52 includes a horizontal bed 54 having a vertical side member 56 attached thereto. A pillow 58 is located at one end of the bed 54 so that a patient may rest his head comfortably thereon. Straps 60 and 62 are attached to the sides of the cot 52 and are available to help hold patients securely on the cot during the scanning process. As noted earlier, motion of the patient during testing is detrimental to precision detection of the patterns of radiation.

Electrical wires 51 and 53 transmit various signals to the detecting means 11 and support means 13 for appropriate actuation of the systems as described hereinafter. A manual control 55 is available to govern the movements of the detecting means 11 and support means 13.

As seen in FIG. 1, the detector head 30 moves along the length of the cot 52 on the rails 12 and 14 during a scan. Previously, it was necessary to move the detector head 30 beyond the cot 52 in order to have adequate viewing of the section of radiation in question. This invention has the advantage of not requiring additional space beyond the support means 13 with the accompanying loss of space utilization and potential conflict with the overhanging detector head 30.

Figure 2:
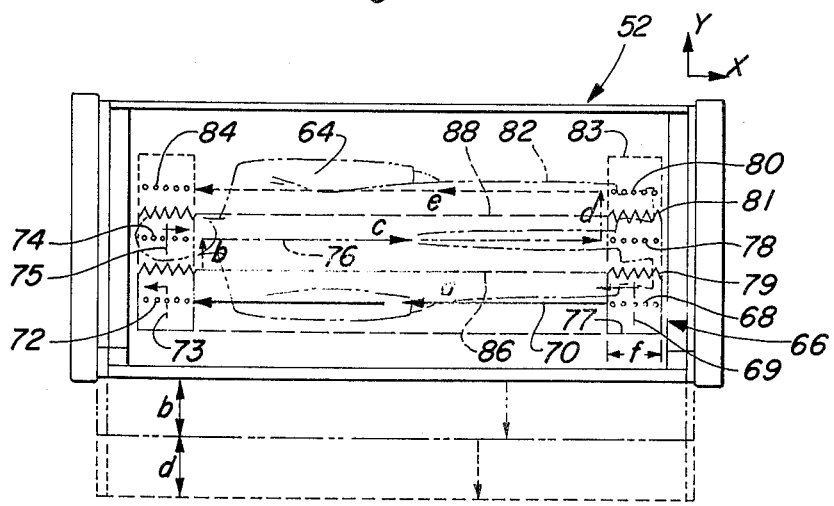
FIG. 2 is a schematic representation of the process of scanning of this invention.

The process of this invention, as schematically represented in FIG. 2, relates to scanning a section of radiation. The term "section of radiation" may be any of radiation but normally involves at least part and sometimes an entire body of a patient 64. Normally, the patient 64 is administered a small amount of radioisotope which flows throughout his system. The radioisotopes concentrate in different patterns in diseased and healthy tissues and thus give a basis for the detection of diseased tissue. In order to detect the patterns of radiation, an area 66 of interest is selected for observation of either about 22 centimeters × 14 centimeters or 32 centimeters × 22 centimeters. As a practical matter, the area 66 of radiation is selected by masking off part of the signals, either physically or electronically.

Because the scan in this invention begins over (or under the end of the section of radiation of interest, provisions must be made for uniform exposure of the detector head 30. If the scan began with the detector head 30 directly over the end of the section of radiation under consideration and a mechanical movement immediately began, the head would receive less radiation at the ends of the section than the middle section. This is simply because the detector head 30 would be over the ends of the section of radiation for a reduced amount of time. In order to provide the same time of exposure to radiation for the detector head 30, an electronic scan is provided and is represented by the dotted portion of the first pass $a$. The electronic scan is analogous to the sliding lid of a box being opened and is illustrated by the dotted line 69 moving to the left. Only radiation to the right of the line 69 will be ultimately used. The speed of the electronic scan is set to match the speed of the mechanical scan which may range from 0 to 159 centimeters per minute. The electronic scan 68 is completed while the detector head 30 remains motionless.

Upon completion of the electronic scan 68, a mechanical scan illustrated by the arrows 70 begins. During the mechanical scan 70, the detector head 30 traverses the length of the cot 52 or a shorter predetermined length as desired. When the detector head 30 reaches the other end of the cot 52, it stops and an electronic scan 72 takes place which is illustrated by the dotted line 73 moving to the left. The radiation used will be to the left of the dotted line 73. It is also possible, however, to have the lines 69 and 73 move to the right but still use the radiation to the left of the lines. The direction of movement of the scan lines are largely a matter of choice and design. The electronic scan may be analogized to the closing of a sliding lid on a box. Again, the electronic scan 72 is timed to coincide with the velocity of the mechanical scan in order to avoid artifacts. The combination of the two electronic scans 68 and 72, and the mechanical scan 70 is referred to generally as the first pass a.

Figure 3:
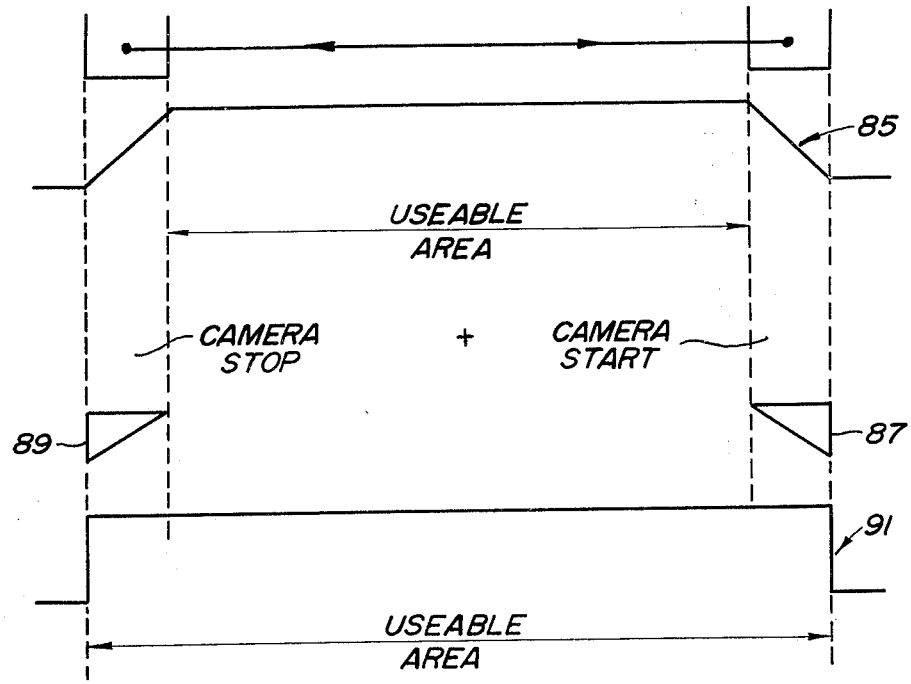
FIG. 3 is a schematic representation of the radiation received during electronic and mechanical scans.

The contribution of the electronic scans are shown in FIG. 3. The height of the graph 85 illustrates the number of events received in a uniform field during a scan to the left. It is quite apparent that the ends of the section of radiation are not exposed uniformly and result in a ramp effect and a diminished useable area. The electronic scans add complementary areas 87 and 89 to the beginning and end of the pass, respectively. The resulting uniform exposure and radiation reception is illustrated in graph 91 and produces an expanded useable area.

As seen in FIG. 2, a single pass of the detector head 30 is not adequate to detect the radiation across the entire width of the section of radiation. Typically, a scan width will be 22 or 32 centimeters depending on the size of the detector head 30. Accordingly, multiple passes are required. In order to make a subsequent pass, the cot 52 is moved transverse to the longitudinal movement of the detector head 30. This transverse movement is illustrated as b and may be termed an indexing of the table. The index or transverse movement b is also shown as the distance of the movement of the table. For purposes of illustration on the section of radiation, FIG. 2 would appear as if the scans move across the patient 64 when, in actuality, it is the patient 64 or the section of radiation that moves relative to the detector head 30. It should be understood, however, the information correlation or blending described hereinafter would also apply if the detector head moved transverse and longitudinal to a stationary cot and/or if the cot moved longitudinal and transverse to a stationary detector head.

After indexing of the table a distance b, an electronic scan 74 again occurs by using only radiation to the left of line 75 as it moves to the right. A mechanical scan 76 and an electronic scan 78 follow. The three scans 74, 76 and 78 make up the second pass c. Similarly, electronic scan 80, mechanical scan 82 and electronic scan 84 make a third pass e after the table has indexed the distance d.

The areas outlined by each pass must be correlated if an accurate representation of the patterns of radiation are to be noted. In particular, the adjacent sides of the scans a and c represented by the dashed line 86 and the adjacent sides of the scans c and e represented by the dotted lines 88 must be exactly correlated or misrepresentations and, therefore, possible mistakes can be encountered.

Figure 3A:
FIGS. 3(A) through 3(D) are schematic representations of the problems of information correlation during multiple scans.

The problem of the correlation of the edges of the passes is represented schematically in FIGS. 3(A) through 3(D). FIG. 3(A) represents a level of photons received in the area of radiation under consideration for a uniform radiation field having a dimension f. That is, the height of FIG. 3(A) indicates that a uniform number of photons are being received across a dimension f of the area of radiation under consideration as seen in FIG. 2. These representations show that no photons are recognized beyond the area of radiation but that all photons are recognized within the area of interest.

Figure 3B:
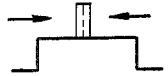

If the area of interest is basically shaped as a rectangle and the adjacent edges of the passes overlap slightly, the result in shown in FIG. 3(B). As noted there, there will be an indication of twice the actual number of photons for any given section of radiation. This would result in a line throughout the entire final readout of the radiation. This overlap could hide representations of diseased tissue.

Figure 3C:
Figure 3D:
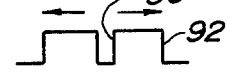

If the rectangular representations could be matched, the ideal would be the representation shown in FIG. 3(C) where there would be a constant number of photons across both passes. If however, the passes are slightly separated from one another, there would be a gap as shown in FIG. 3(D). Thus, accurate detection of radiation patterns and diagnosis of tissue is hindered by misregistration of the areas. In order to overcome the problems illustrated in FIGS. 3(A) through 3(D), this invention proposes the oscillation or modulation of the edges of the rectangle which will be adjacent to each other in the multiple pass situation. This modulation eliminates the distinct lines of the sides of the rectangles and is schematically represented in FIG. 2 as sides 77, 79, 81 and 83 which would extend the length of the scan. Absolute accuracy in registration of adjacent passes thus becomes less critical and if slight variations do occur, will not result in any significant misrepresentations of the patterns of radiation or artifacts.

Detecting Means

Figure 5:
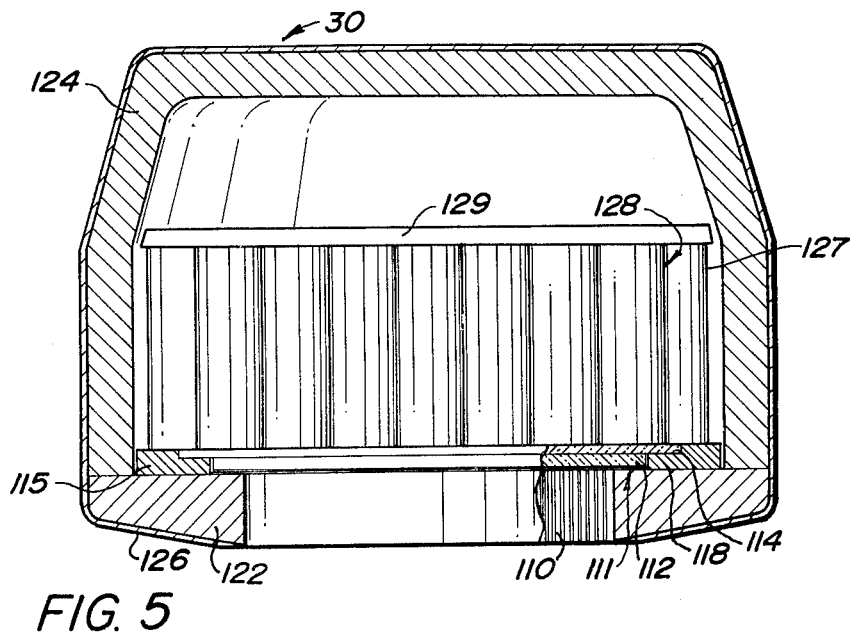
FIG. 5 is a cross-sectional view of the detector head of the scintillation camera.

As used herein, detecting means includes some or all of the apparatuses shown in FIGS. 1, 4, 5, 9 and 9(A). As illustrated in FIG. 5, the detecting means includes the detector head 30 which has a means for forming a visible response from radiation including a collimator 110 and a scintillator 111 immediately above it. The scintillator 111 includes a relatively thin circular scintillation crystal 112 of about ½ inch thickness which is adhered to means of an epoxy to a thin glass plate such as pyrex 114. The glass plate is normally from ¼ inch to ¾ inch thick, but other thicknesses are possible. The scintillation crystal 112 changes invisible radiation, such as gamma radiation, to visible radiation or light radiation (photons). The glass 114 extends beyond the scintillation crystal 112 forming an annular seat 118 which holds the scintillation crystal 112 on a support 115. The scintillator 111 is a type commercially available.

Lead shielding 122 and 124 around the complete interior portion of the detector head 30 prevents the entrance of stray radiation to the scintillator 111. A casing 126 surrounds and supports the entire lead shielding.

Means for converting the light radiation to electrical impulses includes a hexagonal array of photomultiplier tubes 128. The hexagonal arrangement shown in cross-section in FIG. 5 would typically include 37 2 inch photomultiplier tubes viewing the scintillator 111. Variations are possible, however, and 19 3 inch photomultiplier tubes could encompass about the same area. A larger, wide-view detector head is also available and uses 37 3 inch photomultiplier tubes. The additional increase in area reduces the number of passes required for scans of different sections of radiation. The array of photomultiplier tubes 128 is enclosed by a cylindrical light shield 127 formed from sheet metal. A hold-down plate 129 formed from sheet metal is releasably connected to the top of the shield 127.

As noted in FIG. 5, the photomultiplier tubes 128 are placed substantially adjacent to the scintillator 111 with only standard optical coupling grease therebetween. Substantially adjacent, as used herein, means a distance from the scintillator 111 where spatial distortion is a problem. Spatial distortion is a problem well known in the art and is, briefly, that situation where the representation of gamma radiation will appear as if located in a place displaced from its real location. In their present location, however, the photomultiplier tubes sense a maximum number of photons given off by the scintillator 111 and thus improve resolution. In general, it is necessary that the photomultiplier tubes are positioned on one side of the scintillator 111 in order that three (3) of the photomultiplier tubes view a common scintillation.

The detecting means further includes the stand and apparatus for moving the detector head 30 as illustrated in FIG. 1.

Support Means

Figure 6:
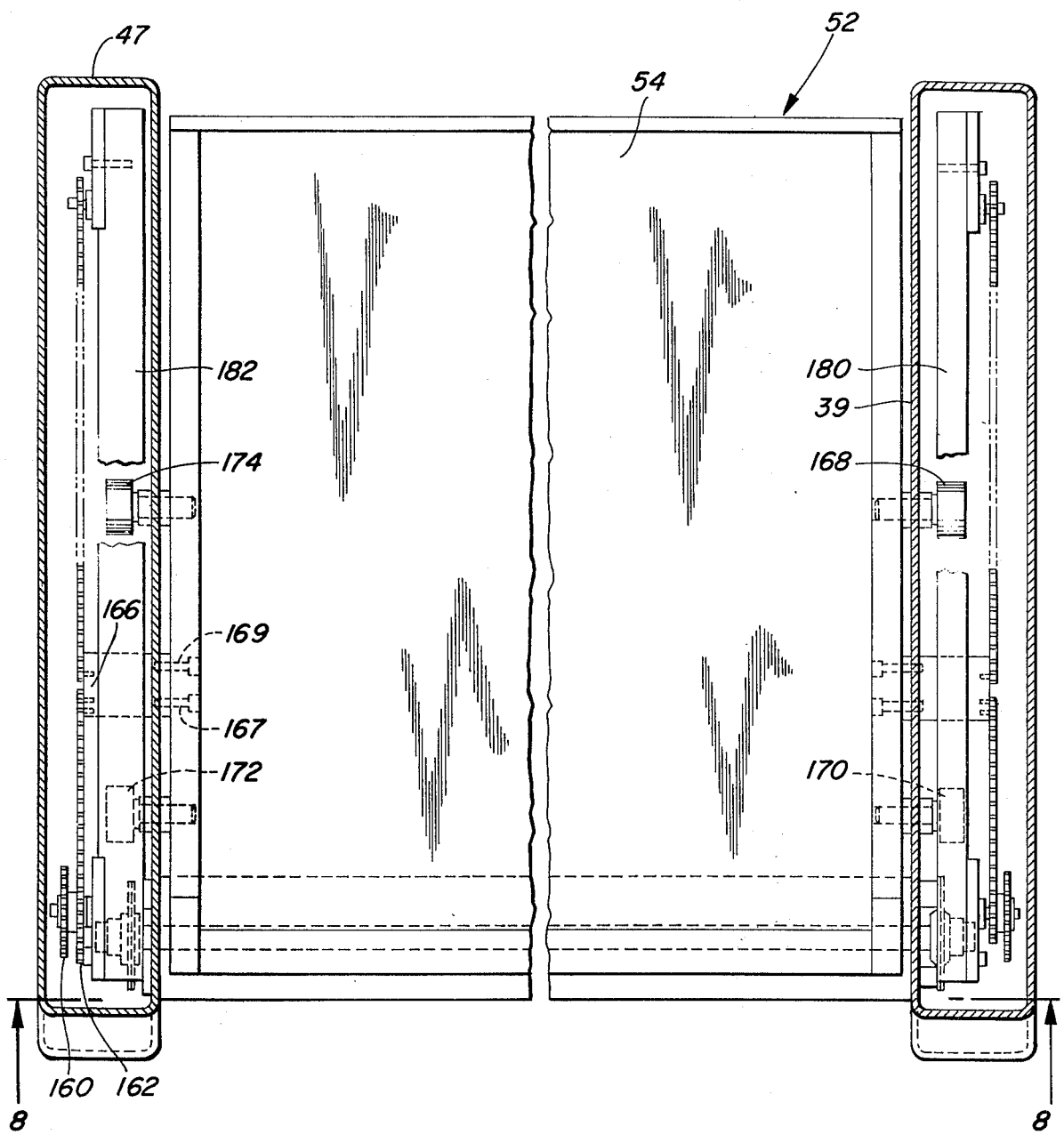
FIG. 6 is a sectional 6—6 of FIG. 1 and shows some of the mechanism for moving the cot.
Figure 7:
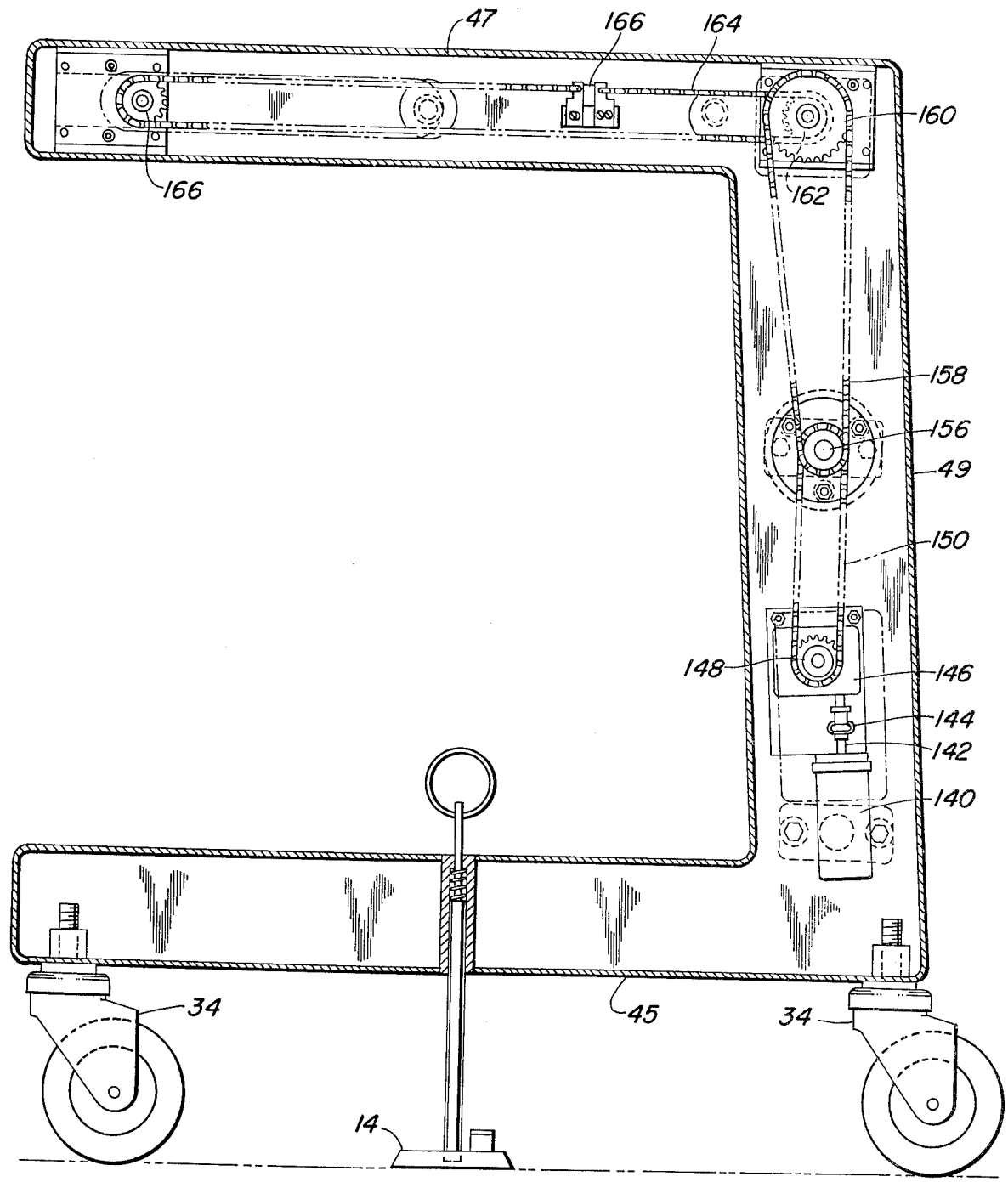
FIG. 7 is a sectional 7—7 of FIG. 1 and represents the mechanism for moving the cot.
Figure 8:
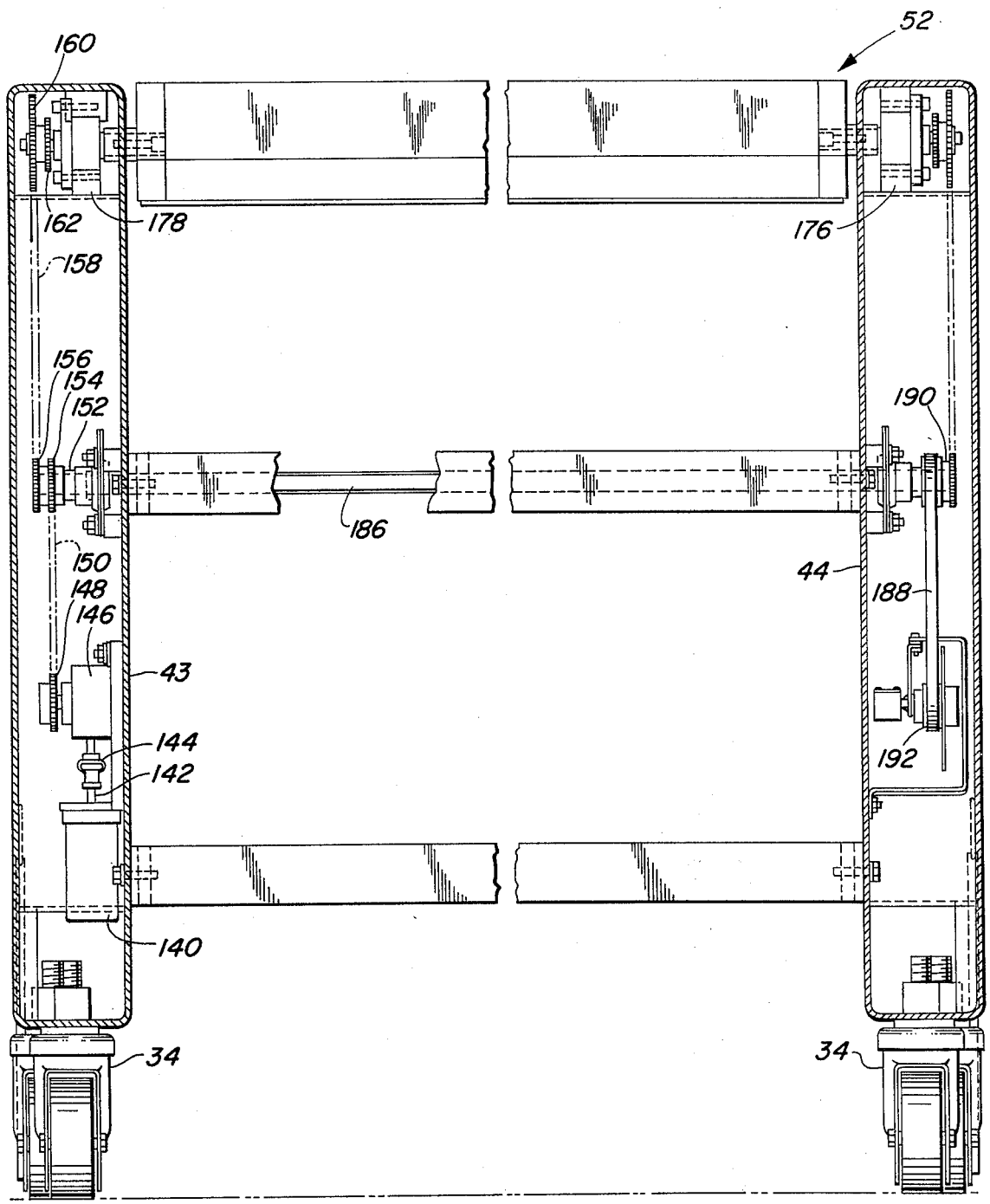
FIG. 8 is a sectional 8—8 of FIG. 1 and is a cross-sectional view of the mechanism for moving the cot.

The support means 13 in FIG. 1 is illustrated in more detail in FIGS. 6, 7 and 8 which represent sections 6—6, 7—7 and 8—8, respectively, of FIG. 1. As shown therein, a motor 140 in the vertical member 43 is connected by means of a shaft 142 and coupling 144 to a drive unit 146. A sprocket 148 is connected to the shaft from the drive unit 146 and actuates a chain 150 which is operatively connected to and drives a shaft 152 by means of the sprocket 154. Another sprocket 156 drives a subsequent inter-connected chain 158 to a sprocket 160. The size of the sprockets are varied in order to obtain the desired power and speed. These sizes are not critical and will be obvious to one skilled in the art. The sprocket 160 is operatively connected to a sprocket 162 which drives a horizontal chain 164 in the horizontal member 47. A block drive 166 is connected to the cot 52 by rods 167 and 169 which pass through a slot in the member 47. The chain 164 interacts with the sprocket 166 operatively attached to the cot 52. Rollers 168, 170, 172 and 174 support the cot 52 on rails 176 and 178 and are themselves held in position by guides 180 and 182.

As particularly noted in FIG. 8, a power shaft 186 transmits torque to a positive drive belt 188 through sprocket 190 to a limiting device 192 which stops the cot 52 from moving beyond its guides. Very similar sprocket and chain drive arrangements are located within the vertical member 44 and horizontal member 39 in order to supply motivating power to the cot 52 on both sides equally and thus avoid any binding or twisting of the cot 52 during motion. Different mechanical devices and their connections, such as the nuts, bolts, caster, the the like, are common and no specific description is felt necessary.

Means for Operating

Figures 9, 10:
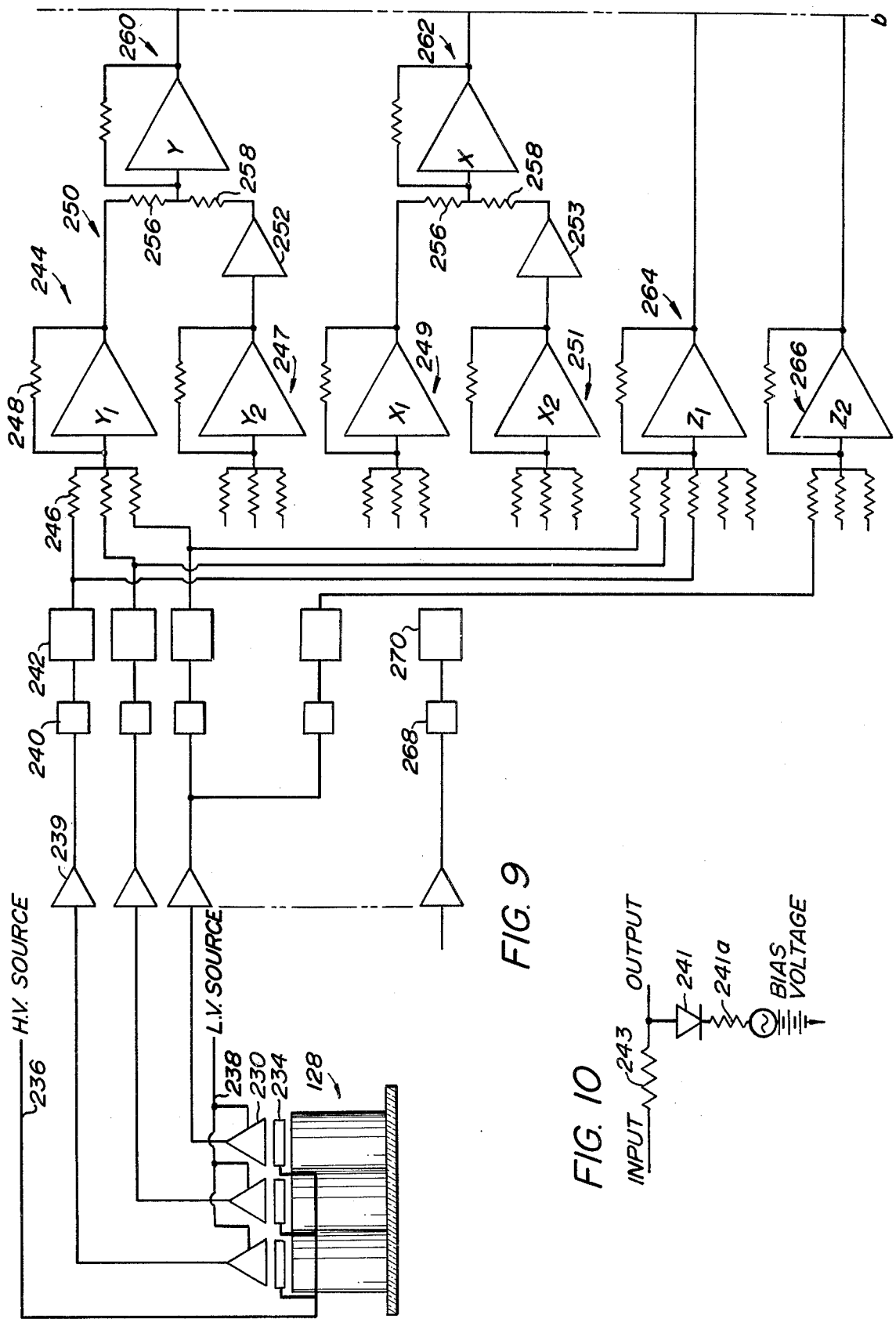
FIGS. 9 and 9(A) are block diagrams of the means for operating on signals in order to produce representations of the location of radiation.
FIG. 10 is a circuit diagram of the biasing means to correct for certain distortions.
Figure 9A:
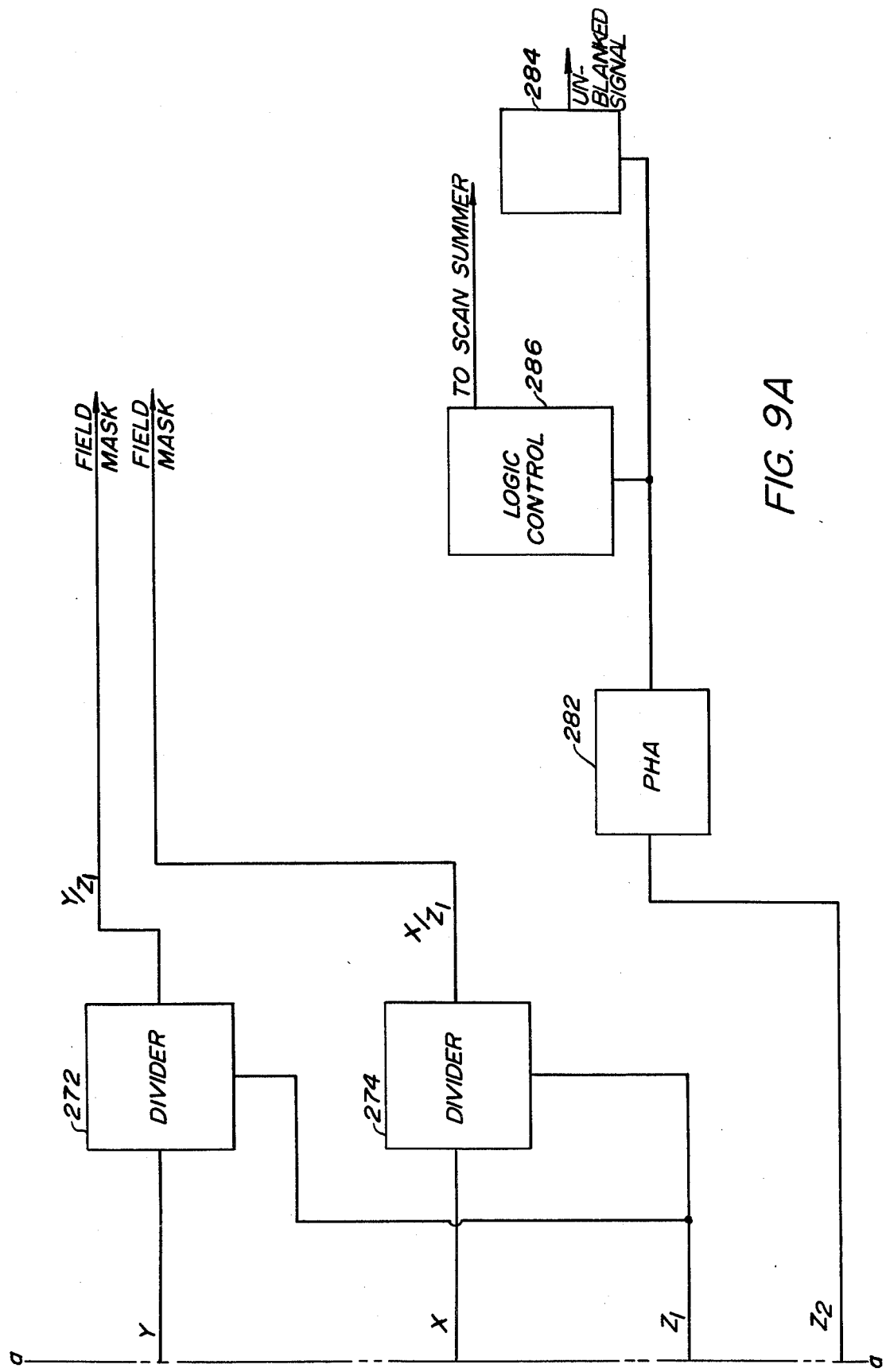

The means for operating on the electrical responses create a signal which gives an indication of the relative location of the radiation and refers, in general, to the circuitry shown in FIGS. 9, 9(A) and 10. It should be understood that variations will be obvious to one skilled in the art. The block diagram in FIGS. 9 and 9(A) showing the major components illustrates that the photomultiplier tubes 128 are connected to resistor divider networks 234 which are fed by a high voltage source 236. The high voltage source 236 is variable depending on the isotope that is used with the camera or static imaging device, as it is alternately called. Preamplifiers 230 receive signals from the photomultiplier tubes and are attached to a low voltage source 238. The preamplifiers 230 provide signals to delay line amplifiers 239. The incoming pulses to the delay line amplifiers 239 are about 3 volts and have a relatively fast rise time of about 750 nanoseconds and an output decay time in the order of about 35 microseconds. The delay line amplifiers 239 shape the pulses so that they have a flat top with a duration of about 2 microseconds. The height of the top of the square wave is directly proportional to the peak of the original pulse. The delay line amplifiers 239 are used in order to give the circuitry time to operate on the pulses and reduce the effects of pulse pile up at high pulse rates. Delay amplifiers have been found preferable to simple pulse stretchers since they reduce dead time. Dead time is defined as the time between signals to which the circuitry can respond. The use of delay amplifiers has permitted dead time as small as 2 microseconds.

Operatively connected to the delay amplifiers output is an initial attenuator 240 which is a diode in parallel with a resistor and is grounded by another resistor. The initial attenuator discriminates against noise or very small signals. The threshold voltage of the diode prevents any signal from passing through it until the signal is of a predetermined value. By discriminating against small signals, utilization is made of only the relatively strong signals which can be used to determine the position of the scintillation in the scintillator more accurately. More details of the initial discriminator are set forth in the above-noted applications.

Operatively connected to the initial discriminator 240 is a means for correcting distortion which results from placing the photomultiplier tubes substantially adjacent or close to the scintillator or from other causes. This means for correcting distortion 242 is illustrated specifically in FIG. 10 and includes an input including a resistor 243 of about 100 ohms, a diode 241 having about 0.6 volts threshold voltage and a resistor 241a of about 60 ohms which leads to bias D.C. voltage of about 0.3 volts and an A.C. bias voltage of about 0.8 volts peak to peak at 60 Hz. The values given are typical values and may be varied. The combined D.C. and A.C. bias voltages are used to increase the uniformity of the field. It was found that a pure D.C. bias voltage caused a diode conduction point which was too abrupt. When the diodes began to conduct, artificial areas of activity under the photomultiplier tubes were noticeable in the pattern. The use of an A.C. and D.C. bias voltage gives a range of threshold values at which the diode begins to conduct. The effect of the diode conduction is thus spread out so that uniformity is vastly improved and the areas under the photomultiplier tubes do not appear as areas of increased activity.

The bias improvement is highly significant since it improves uniformity. It is precisely non-uniformity of radioactive patterns that is a sign of diseased tissue. It is very important, if not critical, to have accurate areas of increased radioactivity which are due to tissue characteristics.

The diode 241 and resistor 241a are placed in parallel with the output from the diode of the biasing unit. Any voltage at the input has its current pass through resistor 243. If the voltage is not above the combined bias and threshold voltage, no current passes through the diode 241. At this point, the output will be directly proportional to the input. As the input voltage is increased, a value is reached where the diode 241 becomes forward biased. At this point, current flows through the diode 241 and resistor 241a and the output voltage is not directly proportional to the input voltage. Thus, the diode 241 and resistor 241a become an attenuating factor in the circuit. The bias voltage is adjustable and may be used to vary the output of the photomultiplier tubes that is transmitted in the circuitry. By using an A.C. bias voltage, spatial distortion and non-uniformity of the field can be virtually eliminated whether the photomultiplier tubes are adjacent to or spaced from the scintillation crystal. Non-linear response devices other than a diode bias could be used to correct for distortion and non-uniformity of field, such as a transistor.

Operatively connected to the diode bias device 242 are summing circuits 244. Summing circuits 244 include subgroup summing amplifier 245 which has input resistor 246 having values of about 5 to 40K ohms and resistor 248 which as a value of about 5K ohms. By way of example, the subgroup summing amplifier 245 for the Y1 signal includes inputs from the photomultiplier tubes on one side of the X axis. For convenience, this shall be noted as the Y1 summing amplifier. Shown in a representative fashion are the summing amplifiers for the Y2 signal, the X1 signal and X2 signal. These subgroup summing amplifiers receive signals from the photomultiplier tubes on either side of the X and Y axis. In particular, the Y1 and Y2 summing amplifiers receive signals from the photomultiplier tubes on either side of the X axis. The X1 and X2 summing amplifiers receive signals from the photomultiplier tubes on either side of the Y axis.

The term "subgroup summing amplifiers" is used to refer generally to the summing amplifiers 245, 247, 249 and 251. In addition to the elements referred to generally as 250, these elements include inverters 252 and 253 and summing amplifiers 260 and 262. The inverters 252 simply change the signal of Y2 and X2 to a negative value before adding them to Y1 and X1, respectively. The usual type resistors 256 and 258 are utilized in the summing amplifiers and have a value of about 5K ohms.

Summing amplifiers 260 and 262, respectively, further combine the signals in a coordinate signal of the Y and X position of the scintillation occurring in the scintillator 211. The photomultiplier tube in the center of the hexagonal array is not operatively connected to the subgroup summing amplifier. Moreover, any photomultiplier tubes which may be on the X axis are not used to determine the Y coordinate position.

The means for operating on the electrical responses further includes the first and second total summing amplifier. The first total summing amplifier 264 is similar to the others described above except that it is operatively connected to all of the photomultiplier tubes. It sums all of the signals after they have been corrected by means of the diode bias device 242, but before they pass into the subgroup summing amplifiers. The resultant signal is referred to as a Z signal.

A second total summing amplifier 266 similarly sums all of the outputs from all of the photomultiplier tubes and gives a $Z_2$ signal. The second total summing amplifier 266 receives its signal from a point before the initial discriminator 240 but after the delay line amplifiers 239. Separate diode bias devices 268 and 270 (similar to that previously described as 240 and 242) are used in conjunction with the second total summing circuit.

As illustrated in FIG. 9(A), the Y, X, $Z_1$ and $Z_2$ signals are then transmitted in the circuitry. In particular, the Y and X signals are transmitted to divider circuits.

The divider circuits are well known elements which take two inputs and divides them. The purpose of the divider circuits is to normalize the coordinate signals and are referred to herein as means for normalizing the Y and X signal to make them independent of the intensity of the scintillation. As illustrated in FIG. 9(A), the Y and X signals are divided by the output of the first total summing amplifier which is the $Z_1$ signal. Thus, the Y and X signals are divided by a denominator which is proportional to the total energy of the scintillation and thus are normalized or made independent of such energy. From the divider circuits, the normalized coordinate signals are then transmitted to the X and Y axis of an oscilloscope 276 having plates 278 for the X axis and plates 280 for the Y axis.

The $Z_2$ signal, which is proportional to the total energy level of the signals viewed by the photomultiplier tubes, is passed through a pulse height analyzer 282. The pulse height analyzer 282 determines the acceptable energy levels of the pulses and is operatively connected to the oscilloscope 276. If the signal is acceptable by the pulse height analyzer 282, it travels to a Z axis driver 284 which is simply a well known element to give a specific time duration to the acceptable pulse. If desired, a logic control 286 may be utilized in the circuit to either give a specific time period for the circuit to operate or to count the number of scintillations before it turns itself off. The normalized Y and X signals and the unblanked signals are transmitted the means for scanning in FIG. 4.

In operation, a radiosistope is given to a patient which forms a radioactive pattern. The radiation, usually gamma rays, pass through the collimator 210 to the scintillator 211. The gamma radiation is thereby changed to visible radiation and is noted by the adjacent photomultiplier tubes. The photomultiplier tubes give electrical signals which are somewhat distorted as a function of position because of the photomultiplier tubes' immediate proximity to the scintillator 211. In other words, the relation of the electrical impulses to the location of radiation in the scintillator is distorted or non-linear. Means for operating on the electrical responses includes appropriate amplifiers and, in particular, a diode bias which gives a non-linear response to an input. The diode bias may be adjustable and is used to remove spatial distortion and non-uniformity of field by varying the output of the photomultiplier tubes to accurately reflect the location of the scintillation. Subgroup summing circuits are operatively connected to the diode biasing means and give a coordinate signal of the location of the scintillation in the scintillation crystal. Coordinate signals are normalized by dividing into them the resultant output of a total summing amplifier. It is recognized and understood that other well known means may be used for summing the output of the photomultiplier tubes and for normalizing them. A second total summing amplifier is used as a pulse height analyzer so that only desirable signals are utilized to trigger the oscilloscope. By use of the radiation sensing device in the invention, an image placed on the scintillation crystal can be reproduced as an image on the oscilloscope. It is further understood that various electronic devices may be used to give a display other than an oscilloscope.

Other changes in the circuitry and in the display means will be obvious to one skilled in the art, and should be considered a part of this invention.

Means for Scanning

Figure 4:
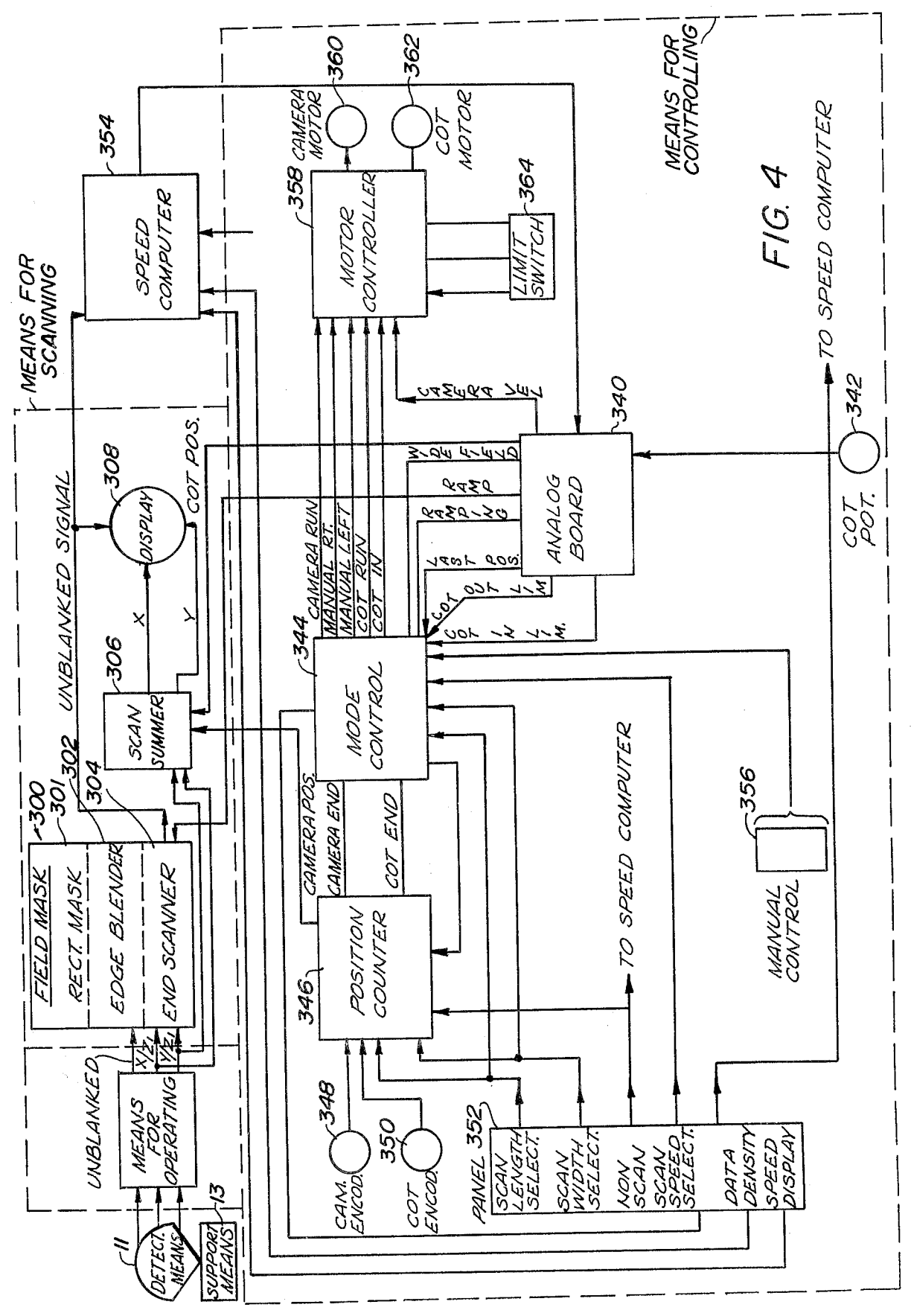

As illustrated in FIG. 4, in block diagram form, the means for scanning receives signals $X/Z_1$, $Y/Z_1$ and the unblanked signal resulting from $Z_2$ and is made up of an electronic field mask 300 which includes a rectangular mask 301, edge blender 302 and end scanner 304. The field mask 300 is operatively connected to the scan summer 306 and display 308. The edge blender 302 and end scanner 304 are variations of the rectangular mask 301 which, as used herein, means an area of radiation that is operated on and accepted for display as defined by certain limits which will be more specifically defined hereinafter. Basically, the rectangular mask 301 is a set of X and Y coordinates inside of which signals will be accepted for display and outside of which they will not be accepted. The rectangular mask 301 defines a rectangular display area although other shapes are possible. As shown in FIG. 2, the area of interest is moved over the section of radiation.

Figure 11:
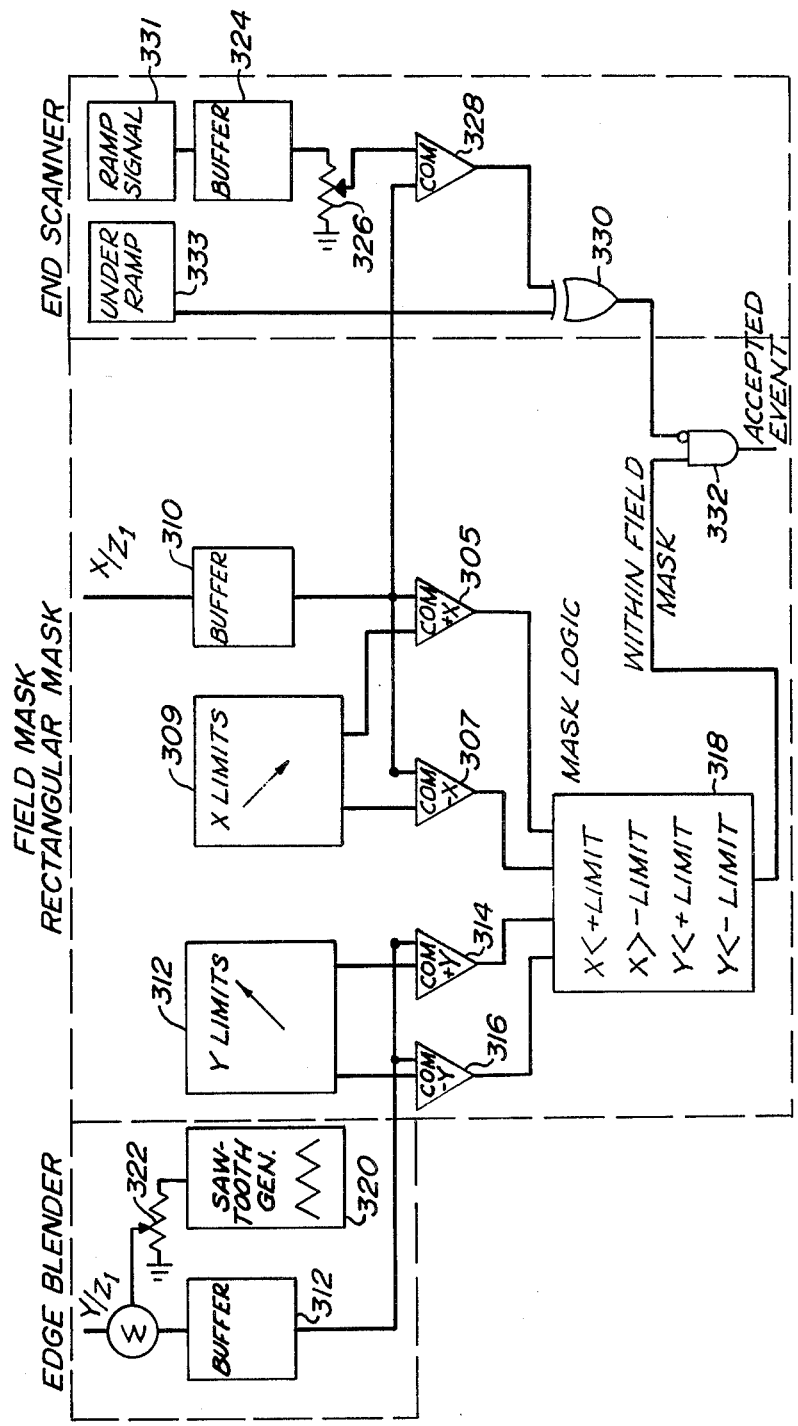
FIG. 11 is a block diagram of the electronic mask for isolating signals of interest.

The field mask 300 is shown more specifically in FIG. 11. Modified signals received from the circuitry of FIGS. 9 and 9(A), as normalized X and Y signals, are fed into buffers 310 and 312, respectively. The buffered normalized X signal is then compared with preset-voltage reference coordinates from a voltage generator 309 by means of a comparator 305 and 307. The present X coordinates are symmetrical about a reference voltage which may be zero voltage or another value. The buffered X signal is compared with the plus X reference voltage and if it is less than the plus X signal, it is passed to a mask logic 318 which is simply a type of comparator. Similarly, the normalized X signal is compared with the minus X signal to see if it is greater than the minus X signal and, therefore, acceptable.

An analogous comparison is made with the Y signal. A Y reference voltage generator 312 generates a signal which is split into symmetrical minus Y and plus Y components. Comparators 314 and 316 are used to compare the reference signals with the normalized Y signal. If the normalized Y signal is less than the plus Y signal and greater than the minus Y signal, appropriate signals are sent to the mask logic 318. If a signal meets all the criteria of the electronic field mask, it passes the signal to a display if no end scans are taking place.

As described above, edge blending is necessary in order to correlate the edges of the passes by the detecting means 11 so that artifacts do not occur. The edge blender 302 shown in dotted in FIG. 11 adds a variable voltage from a saw-toothed generator 320 through a variable resistor 322 in order to adjust for the amount of voltage desired. The saw-toothed wave is added to the Y component which corresponds to the longitudinal movement along the cot 52 and eliminates the distinct edge of the rectangular photon reception as shown in FIG. 2. Because of the fluctuating edge, the information from the various passes can be combined without any substantial artifacts and thus provides accurate representation of the radiation pattern viewed by the detector head 30. The saw-toothed generator 320 gives a voltage having a frequency of 300 Hz and an amplitude of about 10 volts peak to peak although variations in each of these will be obvious as long as they do not themselves provide any artifacts. It is also anticipated that shapes other than the saw-tooth is possible although this configuration has provided the best results.

The end scanner 322 provides the electronic scan at either end of the mechanical scan by varying a scan line parallel to the Y axis from an X limit of the field mask 300. At the moment the pass is actuated, there are no acceptable X limits and no signal is accepted. In correspondence with the scan speed, the scan line (by means of a ramp voltage) is varied in such a manner that more signals gradually become acceptable until the full width of the rectangular scan area is open. This movement of the acceptable X limits are illustrated in FIG. 2 by moving lines 69, 73 and 75. In operation, a signal which is gradually increased is shown as a ramp signal 331 and increases from about minus 5 volts to plus 5 volts. A buffer 324 transmits the signal through a potentiometer 326 so that the limits of the ramp signals can be varied in order to correspond with the full width of the rectangular scan area to a comparator 328. A buffer 310 is connected to the comparator 328 in order to compare it with the changing X ramp voltage. In effect, there is a sweep in the X direction of the scan lines from an X limit for events to be accepted and displayed. This is the analogous situation to the sliding lid of a box being opened until it reaches its full width at which time the entire box starts to move. The output from the comparator 328 goes to an exclusive Orgate 330. An under-ramp generator 333 signal feeds into the exclusive Orgate 330 and is used to determine which side of the sweeping axis will be utilized for display during the electronic end scans. The exact circuitry to accomplish this can be of different types and will be obvious to one skilled in the art. The under-ramp signal is normally a digital voltage which determines which signals will be accepted depending upon the direction of the pass. For example, in a first pass from right to left, as shown in FIG. 2, the field mask would start as a line and gradually open to the area shown as expanded in rectangle. The accepted events will be to the right of the traversing X axis 69. At the end of the first pass, the accepted events will be to the left of the traversing X axis as shown as dotted line 73. During the second pass c, the X axis 75 will move to the right and the acceptable events will be to its left with the opposite effect at the end of the second pass. Thus, the acceptable events have to change with reference to the moveable scanning sides of the rectangle. This variation is taken care of by the under-ramp signal and the exclusive Orgate 330.

During the electronic scans, acceptable signals pass through the exclusive Orgate 330 and the Andgate 332. If the acceptable signal is within the field mask and on the correct side of the moving coordinate axis, the Andgate 332 permits the event to be displayed. During the mechanical scans, when the end scanner is not operative, all events within the field mask will pass through the Andgate 332 to become an accepted event.

The ramp signal generator 331 on the end scanner, as noted earlier, ramps up, i.e., it causes an increasing linear voltage from a minus 5 to about a plus 5 volts. The actual limits of the ramp are used to determine the amount of time of the electronic scan to correspond with the mechanical scan. It is also possible, although more complex, to vary the slope of the ramping signal. At the end of the first pass, the electronic scan will take place by the ramp signal "ramping down", that is, the ramp signal will go from about a plus 5 volts to a minus 5 volts.

The means for scanning also includes a scan summer 306 which correlates the acceptable signals of interest with the position of the support means 13 and detection means 11 so that the appropriate information can be placed in the proper location and sent to the display 308 which is typically an oscilloscope or a camera.

Means for Controlling

The means for controlling is generally the system utilized in determining the actuation and movement of the various components during the electronic and mechanical scan. The means for controlling is shown in dashed line in FIG. 4 and includes an analog board 304 which is a type of signal generator well known to one skilled in the art to cause the different processes to occur for the multiple passes in a complete body scan. The analog board 340 generates the ramp signal to the field mask. It also is used to determine the speed of the camera and includes, if necessary or desirable, digital-to-analog converters. The speed desired can be signaled either decimal form and converted to binary or simple left in a decimal system. The actual type of signaling, whether decimal or binary, is largely a matter of choice and various types of units and circuits are well known in the art to accomplish this end. The analog board 340 also signals the cot position which it receives from the cot potentiometer 342. The position of the cot at its one of two or three positions is used to vary the output so that a second scan will be offset on the display from the first scan in order to make a unitary display. The analog board 340 is also used as a signaling device to indicate camera velocity as well as the in-and-out limits of the cot and the last position of the cot.

The mode control 344 is a circuit which correlates the input from the analog board 340 with the selections made on a panel by the operator and a position counter 346. The mode control 344 acts as a switching device and has four sequences. The first sequence corresponds to the electronic scan and is a ramp up. After the ramp-up signal is completed, the mode control 344 receives a signal from the analog board 340 and switches to camera run which is the mechanical movement of the detector head 30 relative to the cot 52. The mode control 344 holds the camera run until signaled by the position counter 346 that the mechanical traverses completely. Upon signal from a position counter 346, the mode control 344 switches to ramp-down which corresponds to a closing of the viewable area of interest by the detector head 30. When the ramp-down is complete, the mode control 344 receives a signal from the analog board 340 and switches to cot run which, in effect, moves the cot a distance equal to one dimension of the rectangular area under consideration. However, if the scan is completed and no more passes by the detector head 30 are desired, the analog board 340 will signal the mode control 344 to stop.

A position counter 346 receives information from a camera encoder 348 and a cot encoder 350 which are attached to and give the position of the camera and the cot and compares them with the desired scan length and scan width. An encoder, as used herein, is a commercially available device from Optron Co., Model OPB 300, that records length of travel. It travels along the V-shaped rail of FIG. 1 while attached to the detecting means 11. A control panel 352 is used by the operator to select the length, width, speed, data density and speed display, as desired. An optional item in this invention is the use of a speed computer which utilizes the desired density of photon signals to determine the speed of the movement of the detector head 30 and electronic scans. The speed computer 354 simply converts the desired data density into a physical speed. A manual control 356 can be used to override the movement of the detection means 11 and support means 13. A motor controller 358 accepts signals for movement of the camera and cot and transmits them to the camera motor 360 and cot motor 362. The motors then transmit the appropriate movement through the mechanism hereinabove described. A limit switch assembly 364 stops the cot and camera from moving beyond predetermined locations.

Variations in the circuitry, mechanism and controls will be obvious to those skilled in the art as well as the actual details of the various circuitry.

I claim:

1. A radiation sensing device for scanning a section of radiation on a support means comprising:
    means for detecting radiation and give electrical impulses in response thereto;
    means for operating on the electrical impulses to create a signal which gives an indication of the relative location of the radiation;
    means for scanning the section of radiation including:
    a. means for selecting an area of radiation having a perimeter in which radiation is detected and operated on at any one time to determine its relative location during a scan;
    b. means for varying at least part of the perimeter parallel to the longitudinal direction of a pass of the means for detecting, the means for varying including a means for generating a variable voltage as a signal for a portion of the perimeter of the area of radiation so that the portion of the perimeter is not a distinct edge;
    means for controlling the means for detecting and the means for scanning including means for making multiple passes of the means for detecting relative to the support means for the section of radiation in order that information from the multiple passes over different portions of the section of radiation can be blended along the portions of the perimeters without any substantial artifacts.

2. The radiation sensing device of claim 1 wherein the means for selecting includes an electronic masking circuit including discrimination means against all signals except those falling within predetermined coordinates.

3. The radiation sensing device of claim 2 wherein the discrimination means provides coordinate signals of plus X, minus X, plus Y and minus Y signals and comparator means for these signals with the electrical impulses generated by the radiation.

4. The radiation sensing device of claim 3 wherein the means for varying includes a saw-tooth generator.

5. The radiation sensing device of claim 4 wherein the means for detecting radiation includes a means for forming a visible response from radiation and means for converting the visible responses from radiation to electrical impulses.

6. The radiation sensing device of claim 5 wherein the means for forming includes a scintillator which is substantially adjacent to the means for converting which includes a plurality of photomultiplier tubes thereby causing distortion of the relation of the electrical impulses to the location of the radiation and an increase in resolution; and the means for operating further includes a non-linear means for correcting distortion.

7. The radiation sensing device of claim 3 wherein the means for controlling the sequencing of events operatively connected to the means for scanning includes a mode control which governs the movement of the means for detecting and the support means.

8. The radiation sensing device of claim 7 wherein the means for controlling further includes a position counter operatively connected to the mode control, the position counter recording the position of the means for detecting and the support means.

9. The radiation sensing device of claim 8 wherein the means for controlling further includes a motor operatively attached to the means for detecting.

10. The radiation sensing device of claim 3 which further includes a support means for the section of radiation, the support means including a framework supporting a cot operatively attached to the framework in such a manner that it may move transverse to the direction of the passes of the means for detecting.

11. The radiation sensing device of claim 10 wherein the framework for the support means encloses a system of sprockets, chains and a motor operatively attached thereto in order to actuate the movement of the cot.

12. The radiation sensing device of claim 11 wherein limit means are included within the framework and govern the distance which the cot travels.

13. The radiation sensing device of claim 10 wherein the means for detecting includes a scintillator which receives radiation transmitted through a collimator and changes the radiation to light radiation and a plurality of photomultiplier tubes receiving the light radiation and giving electrical impulses which are indications of the relative location of the radiation;

the means for operating further including a non-linear means for correcting distortion caused by the scintillator being substantially adjacent to the photomultiplier tubes, the means for operating further including summing circuits for all of the photomultiplier tubes and dividers for normalizing the X and Y components of the electrical impulses in order to obtain an accurate indication of the relative location of the radiation.

14. The radiation sensing device of claim 13 which further includes a display means for the responses received from the means for scanning.

15. A radiation sensing device for scanning a section of radiation comprising:

means for detecting radiation and giving electrical impulses in response thereto;

means for operating on the electrical impulses to create a signal which gives an indication of the relative location of the radiation;

means for scanning the section of radiation including:

a. means for selecting an area of radiation having a perimeter in which radiation is detected and operated on at any one time to determine its relative location during a scan;

b. means for electronically moving a part of the perimeter in which radiation is detected in such a way that the area of radiation changes thus creating an electronic scan, the means for moving a part of the perimeter including a ramping signal including a linearly changing voltage reference which is compared with the electrical impulses generated by the means for operating so that radiation is only used in a changing area;

means for controlling the means for detecting and the means for scanning including means for moving the means for detecting relative to the section of radiation in order to coordinate the electronic scan and the movement of the means for detecting to avoid any substantial artifacts.

16. The radiation sensing device of claim 15 wherein the means for selecting an area of radiation includes a field mask which discriminates means against all signals except those falling within predetermined plus X, minus X, plus Y and minus Y signals and a comparator for comparing these signals with the electrical impulses generated by the radiation.

17. The radiation sensing device of claim 16 wherein the end scanner further includes an exclusive Orgate and an under-ramp signal means supplying a signal thereto in order to determine which signals are to be accepted for display.

18. The radiation sensing device of claim 17 wherein the means for discriminating further includes an Andgate which accepts signals within the coordinate signals and signals provided as acceptable by the end scanner.

19. The radiation sensing device of claim 18 which further includes an edge blender which generates a varying voltage to the Y components in order to aid in assimilating information from multiple passes.

20. A radiation sensing device for scanning a section of radiation comprising:

means for detecting radiation and giving electrical impulses in response thereto, the means for detecting including:

a. a collimator which transmits radiation, a scintillator on one side of the collimator that changes radiation to light radiation;

means for operating on the electrical impulses to create a signal which gives an indication of the relative location of the radiation;

means for scanning the section of radiation including:

a. means for selecting an area of radiation having a perimeter in which radiation is detected and operated on at any one time to determine its relative location during a scan;

b. means for varying at least part of the perimeter of the area of radiation being operated on, the means for varying including a means for generating a variable voltage as a signal for a portion of the perimeter of the area of radiation so that the portion of the perimeter is not a distinct edge;

c. means for electronically scanning the ends of the section of radiation;

the means for selecting, means for varying and means for electronically scanning being included in a field mask which generates coordinate signals which determine an area in which the electrical impulse will be utilized in obtaining the information from the radiation;

means for controlling the means for detecting and the means for scanning including means for making multiple passes of the means for detecting relative to the section of radiation in order that the information from the multiple passes over different portions of the section of radiation can be blended along the portions of the perimeters without any substantial artifacts and without extending the means for detecting beyond the section of radiation.

21. The radiation sensing device of claim 20 wherein the means for varying at least part of the perimeter includes a saw-tooth generator applied to coordinate signals generally parallel to the direction of travel of the means for detecting.

22. The radiation sensing device of claim 21 wherein the means for electronically scanning includes a ramp signal which varies the coordinate signals transverse to the direction of movement of the means for detecting in order to obtain uniform exposure for the scintillator to the section of radiation.

23. The process of scanning a section of radiation comprising:
   detecting radiation and giving electrical impulses in response thereto;
   operating on the electrical impulses to give an indication of the relative location of the radiation;
   selecting an area of radiation of interest having a perimeter in which radiation is detected and operated on to determine its relative location at any one time;
   varying at least part of the perimeter of the area of radiation being operated on so that the part of the perimeter is not a distinct edge;
   making multiple passes of the area of radiation relative to the section of radiation; and
   blending the varying parts of the perimeters of the areas in order to reduce artifacts as a result of combining areas of radiation of interest during the multiple passes.

24. The process of scanning a section of radiation of claim 23 wherein scanning the section of radiation includes making a first pass with the area of radiation of interest relative to the section of radiation in a first direction while detecting radiation;
   moving the section of radiation relative to the area of radiation in a second direction transverse to the first direction;
   making a second pass with the area of radiation relative to the section of radiation substantially parallel to but offset from the first path.

25. The process of scanning a section of radiation of claim 24 wherein selecting the area of radiation includes electronically masking the electrical impulses so that only radiation within predetermined coordinates will be utilized in the process of scanning.

26. The process of scanning a section of radiation of claim 25 wherein electronically masking includes establishing predetermined electrical signals representing positional locations, comparing the electrical impulses resulting from the radiation with the predetermined electrical signals and displaying only those signals within the positional locations.

27. The process of scanning a section of radiation of claim 26 wherein electronically masking includes establishing plus X, minus X, plus Y and minus Y signals within which electrical impulses from radiation will be displayed thereby establishing a rectangular area of radiation.

28. The process of scanning a section of radiation of claim 27 wherein varying at least part of the perimeter of the area of radiation includes applying a saw-tooth wave to the plus Y and minus Y signal which are parallel to the direction of the passes.

29. The process of scanning a section of radiation of claim 28 wherein detecting radiation includes channeling gamma radiation from the source of radiation through a collimator, changing the gamma radiation to light radiation in a scintillation crystal and viewing the light radiation with photomultiplier tubes substantially adjacent to the scintillation crystal which give off electrical impulses in response thereto.

30. The process of scanning a section of radiation of claim 29 wherein operating on the electrical impulses further includes correcting for spatial distortion by means of a non-linear response device, the spatial distortion resulting from the proximity of the photomultiplier tubes to the scintillation crystal.

31. The process of scanning a section of radiation of claim 24 which further includes electronically scanning the section of radiation at each end of the movement of the area of radiation, the electronic scanning including varying one of the signals that determines the area of radiation.

32. The process of scanning a section of radiation of claim 31 in which electronically scanning includes comparing the electrical impulses from the radiation and with a variable input voltage which is timed to coincide with the movement of the area of radiation and using only the signals which have a predetermined relation with the variable input voltage.

* * * * *